United States Patent [19]

Graham et al.

[11] Patent Number: 4,738,929

[45] Date of Patent: Apr. 19, 1988

[54] **PURIFIED CULTURE OF *STREPTOMYCES GALANOSA***

[75] Inventors: Blanche D. Graham, Ann Arbor; Josefino B. Tunac, Troy, both of Mich.

[73] Assignee: Warner-Lambert Company, Morris Plains, N.J.

[21] Appl. No.: 942,556

[22] Filed: Dec. 18, 1986

Related U.S. Application Data

[62] Division of Ser. No. 743,321, Jun. 10, 1985, Pat. No. 4,657,909.

[51] Int. Cl.$^4$ .................. C12N 1/20; C12P 17/12; C12R 1/465
[52] U.S. Cl. .................................. 435/253; 435/122; 435/886
[58] Field of Search ................ 435/253, 886, 122; 514/249

[56] References Cited

U.S. PATENT DOCUMENTS 4,593,097  6/1986  Tomita et al. .................. 435/122

*Primary Examiner*—Elizabeth Weimar
*Attorney, Agent, or Firm*—Jerry F. Janssen

[57] ABSTRACT

Acids, esters, imine acids, imine esters, and imine amides derived from 6-formyl-4,7,9-trihydroxy-1-phenazinecarboxylic acid, methyl ester and from 6-formyl-4,7,9-trihydroxy-8-methyl-1-phenazinecarboxylic acid, methyl ester demonstrate anti-microbial and anti-neoplastic activity.

A purified strain of *Streptomyces galanosa*, NRRL 15738, is capable of producing 6-formyl-4,7,9-trihydroxy-8-methyl-1-phenazinecarboxylic acid, methyl ester in isolable quantities from a fermentation broth containing assimilable sources of carbon and nitrogen.

1 Claim, No Drawings

PURIFIED CULTURE OF STREPTOMYCES GALANOSA

This application is a divisional of U.S. Ser. No. 743,321 filed June 10, 1985, now U.S. Pat. No. 4,657,909.

BACKGROUND OF THE INVENTION

The present invention relates to novel phenazine carboxaldehydes and derivatives having antimicrobial and antineoplastic activity, to methods of preparing the novel compounds, to a purified strain of *Streptomyces galanosa* NRRL 15738 useful in the preparation of starting material for compounds of the present invention, and to a method for the use of compounds of the present invention as antimicrobial or antineoplastic agents.

The present invention also relates to novel compounds useful as intermediates in the preparation of the phenazine carboxaldehyde derivatives of the invention.

Phenazine compounds are known as natural products (see J. M. Ingram, et al, *Adv. Appl. Microbiol.*, 13:267 (1970)), including phenazine-1-carboxamide (oxychloraphine), and methoxylated derivatives of phenazine-1-carboxylic acid (e.g., griseolutin).

Phenazine-1-carboxylic acid has been evaluated as an antitumor agent (see V. Chernetskii et al, *Onkologyia* (Kiev), 5:110 (1974) and O. A. Sidorik et al, *Fiziol. Act. Veshch*, 6:92 (1974)).

Substituted phenazine-1-carboxamides have also been evaluated for antitumor activity, and found active against sarcoma 180 (see K. Katagiri et al, *Kenyu Nempo*, 17:127 (1967)).

Phenazine-1-carboxamides bearing a tetrazole side chain have been evaluated as antiallergy agents (U.S. Pat. No. 4,337,579).

3,4-Benzophenazine-1-carboxamides bearing a variety of side chains including dimethylaminoethyl have been evaluated for antimicrobial activity (see H. Shoji et al, *Yakugaku Zasshi*, 103:245 1982)).

Phenazine-1,4-dicarboxamides bearing alkylamino- and dialkylaminopropyl side chains have been evaluated for antimalarial activity (see S. N. Sawhney et al, *J. Pharm. Sci.*, 68:524 (1979)).

The natural phenazine derivative, lomondomycin (also known in the literature as lomofungin), is reported as being produced in fermentation broths by the microorganism *Streptomyces lomondensis* NRRL 3252 (U.S. Pat. No. 3,359,165) and has been assigned the structure corresponding to 6-formyl-4,7,9-trihydroxy-1-phenazinecarboxylic acid, methyl ester (see C. G. Tipton, et al, *J. Amer. Chem. Soc.*, 92(5):1425–1426 (1970)).

SUMMARY OF THE INVENTION

In its broadest aspect, the present invention provides compounds having the structural Formula I

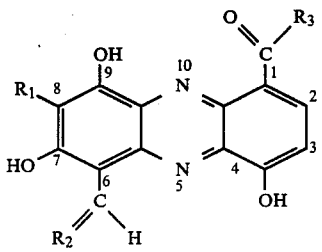

wherein $R_1$ is hydrogen or methyl; $R_2$ is oxygen, or $=N-Y-NR_4R_5$, where Y is cyclohexyl or a straight or branched alkylene group of from one to six carbons optionally substituted with hydroxyl; $R_4$ and $R_5$ are independently hydrogen, alkyl of from one to four carbon atoms, optionally substituted with hydroxyl; or alternatively, $R_2$ is $=N(CH_2)_n-W$ where n equals zero to four and W is a pyrrolidinyl or piperidinyl ring optionally substituted with alkyl of from one to four carbon atoms which may be further substituted with hydroxyl; $R_3$ is hydroxy, alkoxy of from one to four carbon atoms, or $-NH-Y'-NR_4'R_5'$ where Y' is cyclohexyl or a straight or branched alkylene group of from one to to six carbon atoms optionally substituted with hydroxyl; and $R_4'$ and $R_5'$ are independently hydrogen, alkyl of from one to four carbon atoms, optionally substituted with hydroxyl; or alternatively, $R_3$ is $-NH(CH_2)_{n'}-W'$ where n' equals zero to four and W' is a pyrrolidinyl or piperidinyl ring optionally substituted with alkyl of from one to four carbon atoms which may be further substituted with hydroxyl; with the provisos that (a) when $R_2$ is $=N-Y-NR_4R_5$ and $R_3$ is $-NH-Y'-R_4'R_5'$ the groups Y and Y' may be the same or different, $R_4$ and $R_4'$ may be the same or different, and $R_5$ and $R_5'$ may be the same or different, or, alternatively, when $R_2$ is $=N-(CH_2)_n-W$ and $R_3$ is $-NH-(CH_2)_{n'}-W'$ the numbers n and n' may be the same or different and the groups W and W' may be the same or different; and (b) when $R_1$ is hydrogen and $R_2$ is oxygen, $R_3$ may not be hydroxy or alkoxy; and the pharmaceutically acceptable salts thereof.

In another aspect of the present invention there are provided pharmaceutical compositions useful for the treatment of microbial infections in a mammal comprising an antimicrobially effective amount of a compound of Formula I in combination with a pharmaceutically acceptable carrier.

In yet another aspect, the present invention provides a method of treating microbial infections in a mammal comprising administering to a mammal in need of such treatment a pharmaceutical composition comprising an antimicrobially effective amount of a compound of Formula I in combination with a pharmaceutically acceptable carrier.

In another aspect, the present invention provides a method of inhibiting the growth of neoplasms in a mammal comprising the administration to a mammal in need of such treatment a pharmaceutical composition comprising an antineoplastically effective amount of a compound of Formula I in combination with a pharmaceutically acceptable carrier.

In yet another aspect, the present invention provides a pure strain of *Streptomyces galanosa*, designated NRRL 15738, which is capable of producing 6-formyl-4,7,9-trihydroxy-8-methyl-1-phenazinecarboxylic acid, methyl ester in isolable quantities from a fermentation broth containing assimilable sources of carbon and nitrogen under conditions of aerobic fermentation.

In a further aspect, the present invention provides a method of preparing a compound having the structural formula

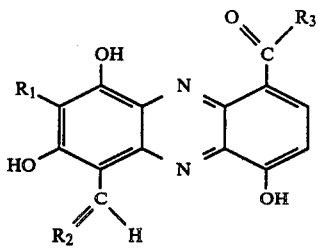

wherein $R_1$ is hydrogen or methyl; $R_2$ is oxygen, or $=N-Y-NR_4R_5$, where Y is cyclohexyl or a straight or branched alkylene group of from one to six carbons optionally substituted with hydroxyl; $R_4$ and $R_5$ are independently hydrogen, alkyl of from one to four carbon atoms, optionally substituted with hydroxy;, or alternatively, $R_2$ is $=N(CH_2)_n-W$ where n equals zero to four and W is a pyrrolidinyl or piperidinyl ring optionally substituted with alkyl of from one to four carbon atoms which may be further substituted with hydroxyl; $R_3$ is hydroxy, alkoxy of from one to four carbon atoms or atoms, or $-NH-Y'-NR_4'R_5'$ where $Y'$ is cyclohexyl or a straight or branched alkylene group of from one to six carbon atoms optionally substituted with hydroxyl; and $R_4'$ and $R_5'$ are independently hydrogen, alkyl of from one to four carbon atoms, optionally substituted with hydroxyl; or, alternatively, $R_3$ is $-NH(CH_2)_{n'}-W'$ where $n'$ equals zero to four and $W'$ is a pyrrolidinyl or piperidinyl ring optionally substituted with alkyl of from one to four carbon atoms which may be further substituted with hydroxyl; with the provisos that (a) when $R_2$ is $=N-Y-NR_4R_5$ and $R_3$ is $-NH-Y'-R_4'R_5'$ the groups Y and $Y'$ may be the same or different, $R_4$ and $R_4'$ may be the same or different, and $R_5$ and $R_5'$ may be the same or different; or, when $R_2$ is $=N(CH_2)_n-W$ and $R_3$ is $-NH(CH_2)_{n'}-W'$, the numbers n and $n'$ may be the same or different, and the groups W and $W'$ may be the same or different; and (b) when $R_1$ is hydrogen and $R_2$ is oxygen, $R_3$ may not be hydroxy or alkoxy; and the pharmaceutically acceptable salts thereof, comprising the steps of (a) reacting a compound having the structural Formula II

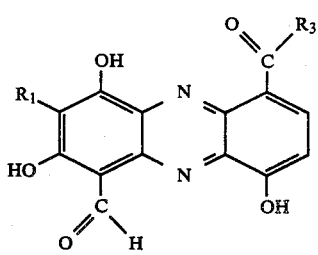

wherein $R_1$ is hydrogen or methyl and $R_3$ is hydroxy or alkoxy with one equivalent of a compound having the formula $R_4R_5N-Y-NH_2$ or $W-(CH_2)_n-NH_2$ where $R_4$, $R_5$, Y, n, and W are as previously defined to form an imine ester or imine carboxylic acid compound having the structural Formula IIIa or IIIb

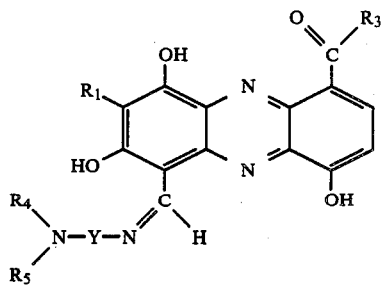

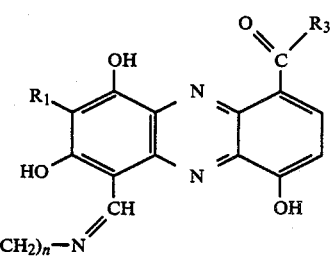

where $R_3$ is hydroxy or alkoxy and Y, $R_4$, $R_5$, n, and W are as previously defined, or (b) alternatively converting a compound of structural Formula II where $R_3$ is methoxy to a higher alkyl ester where $R_3$ is alkoxy of from two to four carbon atoms by conventional transesterification methods and thereafter converting, if desired, the resulting higher alkyl ester to an imine ester of Formula IIIA or IIIB by the process of step (a);

(c) alternatively thereafter saponifying the imine ester product of step (a) or step (b), if desired, with aqueous base to form the corresponding imine carboxylic acid compound; or alternatively (d) reacting the imine ester product of step (a) or step (b) with a compound having the formula $R_4'R_5'N-Y'-NH_2$ where $Y'$ is cyclohexyl or a straight or branched alkylene group of from one to six carbon atoms optionally substituted with hydroxyl; and $R_4'$ and $R_5'$ are independently hydrogen, alkyl of from one to four carbon atoms, optionally substituted with hydroxyl, or with a compound having the formula $W'-(CH_2)_{n'}-NH_2$ where $n'$ equals zero to four and $W'$ is a pyrrolidinyl or piperidinyl ring optionally substituted with alkyl of from one to four carbons atoms which may be further substituted with hydroxyl, to form an imine amide compound having the structural Formula IV

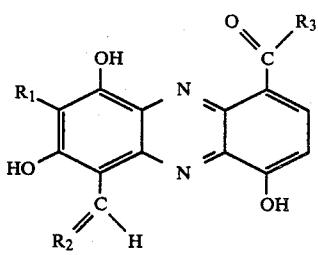

(e) and thereafter hydrolyzing the imine amide product of step (d), if desired, in dilute aqueous acid to form an amide compound having the structural Formula Va or Vb

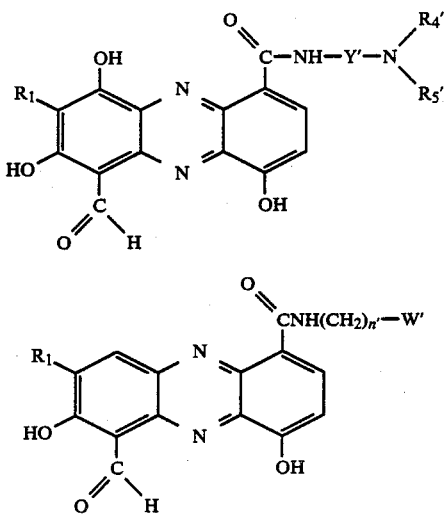

where $R_4'$, $R_5'$, $Y'$, $n'$, and $W'$ are as previously defined; and (f) converting the product of step (a), (b), (c), (d), or (e) to a pharmaceutically acceptable salt, if desired.

DETAILED DESCRIPTION

In accordance with one subgeneric chemical compound aspect, the present invention provides esters of the formula

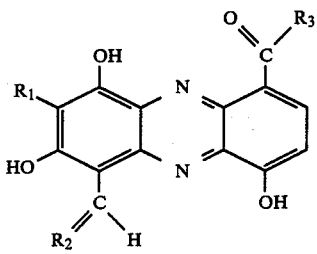

where $R_1$ is methyl and $R_3$ is alkoxy of from one to four carbon atoms.

Particularly preferred is the compound 6-formyl-4,7,9-trihydroxy-8-methyl-1-phenazinecarboxylic acid, methyl ester.

In another aspect, the present invention includes the compound 6-formyl-4,7,9-trihydroxy-8-methyl-1-phenazinecarboxylic acid and its pharmaceutically acceptable salts.

In accordance with another subgeneric chemical compound aspect, compounds of the present invention include imine esters of structural Formula IIIA or IIIB above where the group $R_3$ is alkoxy of from one to four carbons and the imine group is defined as $=N-Y-NR_4R_5$ or $=N(CH_2)_n-W$. The groups $R_4$ and $R_5$ are independently hydrogen or are alkyl or hydroxyalkyl groups of from one to four carbon atoms, or alternatively, when $R_3$ is $=N(CH_2)_n'-W'$, n equals zero to four and W is a pyrrolidinyl or piperidinyl ring optionally substituted with alkyl of from one to four carbon atoms which may be further substituted with hydroxyl.

The linking group Y is cyclohexyl or is straight or branched alkylene of from one to six carbon atoms, optionally substituted with hydroxyl. By the term "alkylene" as used throughout this specification and appended claims is meant a straight or branched hydrocarbon group of the general formula $C_xH_{2x}$ where x is an integer ranging from one to six. When x takes on a value of three to six, one or more of the hydrogen atoms of the linking group Y may be optionally substituted with hydroxyl.

The terms "alkyl" and "hydroxyalkyl" of from one to four carbon atoms as used throughout this specification and the appended claims are intended to include straight chain and branched chain alkyl and hydroxyalkyl groups such as methyl, hydroxymethyl, ethyl, 2-hydroxyethyl, propyl, 2- and 3-hydroxypropyl, 1-methylethyl, 1-(hydroxymethyl)ethyl, butyl, 3-, and 4-hydroxybutyl, and the like.

Particularly preferred groups for $R_4$ and $R_5$ are hydrogen, methyl, hydroxymethyl, ethyl, 2-hydroxyethyl, propyl, 2- and 3-hydroxypropyl.

Examples of group Y include methylene, ethylene, propylene, butylene, pentylene, hexylene, 2-methylbutylene, 2-hydroxypropylene, 2-hydroxy-, and 2,3-dihydroxybutylene, cyclohexyl, and the like. Particularly preferred groups for Y are methylene, ethylene, propylene, 2-hydroxypropylene, and cyclohexyl.

Examples of compounds falling within the scope of this embodiment of the invention include:

4,7,9-Trihydroxy-6-(iminomethyl)-1-phenazinecarboxylic acid, methyl ester.

4,7,9-Trihydroxy-6-(iminomethyl)-8-methyl-1-phenazinecarboxylic acid, methyl ester.

4,7,9-Trihydroxy-6-[(methylimino)methyl]-1-phenazinecarboxylic acid, methyl ester.

4,7,9-Trihydroxy-8-methyl-6-[(methylimino)methyl]-1-phenazinecarboxylic acid, methyl ester.

6-[[(2-Aminoethyl)]imino]methyl]-4,7,9-trihydroxy-1-phenazinecarboxylic acid, methyl ester.

6-[[(2-Aminoethyl)]imino]methyl]-4,7,9-trihydroxy-8-methyl-1-phenazinecarboxylic acid, methyl ester.

6-[[[2-(Dimethylamino)ethyl]imino]methyl]-4,7,9-trihydroxy-1-phenazinecarboxylic acid, methyl ester.

6-[[[2-(Dimethylamino)ethyl]imino]methyl]-4,7,9-trihydroxy-8-methyl-1-phenazinecarboxylic acid, methyl ester.

4,7,9-Trihydroxy-6-[[[2-(1-pyrrolidinyl)ethyl]imino]methyl]-1-phenazinecarboxylic acid, ethyl ester.

4,7,9-Trihydroxy-8-methyl-6-[[[2-(1-pyrrolidinyl)ethyl]imino]methyl]-1-phenazinecarboxylic acid, ethyl ester.

6-[[[4-(Dimethylamino)cyclohexyl]imino]methyl]-4,7,9-trihydroxy-1-phenazinecarboxylic acid, methyl ester.

6-[[[4-(Dimethylamino)cyclohexyl]imino]methyl]-4,7,9-trihydroxy-8-methyl-1-phenazinecarboxylic acid, methyl ester.

6-[[[(1-Ethyl-2-pyrrolidinyl)methyl]imino]methyl]-4,7,9-trihydroxy-1-phenazinecarboxylic acid, methyl ester.

6-[[[(1-Ethyl-2-pyrrolidinyl)methyl]imino]methyl]-4,7,9-trihydroxy-8-methyl-1-phenazinecarboxylic acid, methyl ester.

4,7,9-Trihydroxy-6-[[[2-(1-methyl-2-pyrrolidinyl)ethyl]imino]methyl]-1-phenazinecarboxylic acid, methyl ester.

4,7,9-Trihydroxy-8-methyl-6-[[[2-(1-methyl-2-pyrrolidinyl)ethyl]imino]methyl]-1-phenazinecarboxylic acid, methyl ester.

4,7,9-Trihydroxy-6-[[(1-methyl-4-piperidinyl)imino]methyl]-1-phenazinecarboxylic acid, methyl ester.

4,7,9-Trihydroxy-8-methyl-6-[[(1-methyl-4-piperidinyl)imino]methyl]-1-phenazinecarboxylic acid, methyl ester.

6-[[[5-(Dimethylamino)pentyl]imino]methyl]-4,7,9-trihydroxy-1-phenazinecarboxylic acid, methyl ester.

6-[[[5-(Dimethylamino)pentyl]imino]methyl]-4,7,9-trihydroxy-8-methyl-1-phenazinecarboxylic acid, methyl ester.

4,7,9-Trihydroxy-6-[[2-[(2-methylpropyl)amino]-ethyl]imino]methyl]-1-phenazinecarboxylic acid, methyl ester.

4,7,9-Trihydroxy-8-methyl-6-[[2-[(2-methylpropyl)amino]ethyl]imino]methyl]-1-phenazine carboxylic acid, methyl ester.

6-[[[2-(Diethylamino)ethyl]imino]methyl]-4,7,9-trihydroxy-1-phenazinecarboxylic acid, methyl ester.

6-[[[2-(Diethylamino)ethyl]imino]methyl]-4,7,9-trihydroxy-8-methyl-1-phenazinecarboxylic acid, methyl ester.

4,7,9-Trihydroxy-6-[[[2-(methylamino)ethyl]-imino]methyl]-1-phenazinecarboxylic acid, methyl ester.

4,7,9-Trihydroxy-8-methyl-6-[[[2-(methylamino)ethyl]imino]methyl]-1-phenazinecarboxylic acid, methyl ester.

4,7,9-Trihydroxy-6-[[[2-[(2-hydroxyethyl)amino]ethyl]imino]methyl-1-phenazinecarboxylic acid, methyl ester.

4,7,9-Trihydroxy-6-[[[2-[(2-hydroxyethyl)amino]ethyl]imino]methyl-8-methyl-1-phenazinecarboxylic acid, methyl ester.

6-[[[2-(Ethylmethylamino)ethyl]imino]methyl]-4,7,9-trihydroxy-1-phenazinecarboxylic acid, methyl ester.

6-[[[2-(Ethylmethylamino)ethyl]imino]methyl]-4,7,9-trihydroxy-8-methyl-1-phenazinecarboxylic acid, methyl ester.

6-[[[2-[Bis(hydroxyethyl)amino]ethyl]imino]methyl]-4,7,9-trihydroxy-1-phenazinecarboxylic acid, methyl ester.

6-[[[2-[Bis(hydroxyethyl)amino]ethyl]imino]methyl]-4,7,9-trihydroxy-8-methyl-1-phenazinecarboxylic acid, methyl ester.

6-[[[3-(Dimethylamino)-2-hydroxypropyl]imino]methyl]-4,7,9-trihydroxy-1-phenazinecarboxylic acid, methyl ester.

6-[[[3-(Dimethylamino)-2-hydroxypropyl]imino]methyl]-4,7,9-trihydroxy-8-methyl-1-phenazinecarboxylic acid, methyl ester.

In accordance with another subgeneric chemical compound aspect, compounds of the present invention include imine acids of the structural formula

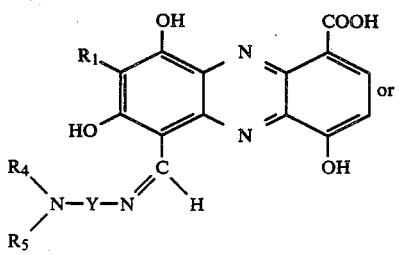

or

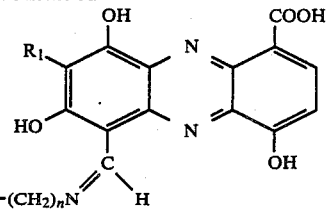

where Y, $R_4$, $R_5$, n, and W have the values defined above.

Examples of compounds falling within the scope of this embodiment include:

4,7,9-Trihydroxy-6-(iminomethyl)-1-phenazinecarboxylic acid.

4,7,9-Trihydroxy-6-(iminomethyl)-8-methyl-1-phenazinecarboxylic acid.

6-[[(2-Aminoethyl)]imino]methyl]-4,7,9-trihydroxy -1-phenazinecarboxylic acid.

6-[[(2-Aminoethyl)]imino]methyl]-4,7,9-trihydroxy -8-methyl-1-phenazinecarboxylic acid.

6-[[[4-(Dimethylamino)cyclohexyl]imino]methyl]-4,7,9-trihydroxy-1-phenazinecarboxylic acid.

6-[[[4-(Dimethylamino)cyclohexyl]imino]methyl]-4,7,9-trihydroxy-8-methyl-1-phenazinecarboxylic acid.

6-[[[(1-ethyl-2-pyrrolidinyl)methyl]imino]methyl]-4,7,9-trihydroxy-1-phenazinecarboxylic acid.

6-[[[(1-ethyl-2-pyrrolidinyl)methyl]imino]methyl]-4,7,9-trihydroxy-8-methyl-1-phenazinecarboxylic acid.

4,7,9-Trihydroxy-6-[[[2-(1-methyl-2-pyrrolidinyl)ethyl]imino]methyl]-1-phenazinecarboxylic acid.

4,7,9-Trihydroxy-8-methyl-6-[[[2-(1-methyl-2-pyrrolidinyl)ethyl]imino]methyl]-1-phenazine carboxylic acid.

4,7,9-Trihydroxy-6-[[(1-methyl-4-piperidinyl)methyl]-1-phenazinecarboxylic acid.

4,7,9-Trihydroxy-8-methyl-6-[[(1-methyl-4-piperidinyl)imino]methyl]-1-phenazinecarboxylic acid.

6-[[[5-(Dimethylamino)pentyl]imino]methyl]-4,7,9-trihydroxy-1-phenazinecarboxylic acid.

6-[[[5-(Dimethylamino)pentyl]imino]methyl]-4,7,9-trihydroxy-8-methyl-1-phenazinecarboxylic acid.

4,7,9-Trihydroxy-6-[[[2-[(2-methylpropyl)amino]-ethyl]imino]methyl]-1-phenazinecarboxylic acid.

4,7,9-Trihydroxy-8-methyl-6-[[[2-[(2-methylpropyl)amino]ethyl]imino]methyl]-1-phenazinecarboxylic acid.

4,7,9-Trihydroxy-6-[[[2-(methylamino)ethyl]imino]methyl]-1-phenazinecarboxylic acid.

4,7,9-Trihydroxy-8-methyl-6-[[[2-(methylamino)ethyl]imino]methyl]-1-phenazinecarboxylic acid.

4,7,9-Trihydroxy-6-[[[2-[(2-hydroxyethyl)amino]ethyl]imino]methyl]-1-phenazinecarboxylic acid.

4,7,9-Trihydroxy-6-[[[2-[(2-hydroxyethyl)amino]ethyl]imino]methyl]-8-methyl-1-phenazinecarboxylic acid.

6-[[[2-(Ethylmethylamino)ethyl]imino]methyl]-4,7,9-trihydroxy-1-phenazinecarboxylic acid.

6-[[[2-(Ethylmethylamino)ethyl]imino]methyl]-4,7,9-trihydroxy-8-methyl-1-phenazinecarboxylic acid.

4,7,9-Trihydroxy-6-[[[2-(1-pyrrolidinyl)ethyl]imino]methyl]-1-phenazinecarboxylic acid.

4,7,9-Trihydroxy-8-methyl-6-[[[2-(1-pyrrolidinyl)ethyl]imino]methyl]-1-phenazinecarboxylic acid.

4,7,9-Trihydroxy-6-[[[2-(1-pyrrolidinyl)ethyl]imino]methyl]-1-phenazinecarboxylic acid.

4,7,9-Trihydroxy-6-[[[2-(1-pyrrolidinyl)ethyl]methyl]-8-methyl-1-phenazinecarboxylic acid.

6-[[[3-(Dimethylamino)-2-hydroxypropyl]imino]methyl]-4,7,9-trihydroxy-1-phenazinecarboxylic acid.

6-[[[3-(Dimethylamino)-2-hydroxypropyl]imino]methyl]-4,7,9-trihydroxy-8-methyl-1-phenazinecarboxylic acid.

In accordance with a further subgeneric chemical compound aspect, compounds of the present invention include imine amides of structural Formula IV above where Y and Y' may be alike or different, $R_4$ and $R_4'$ may be alike or different and $R_5$ and $R_5'$ may be alike or different, n and n' may be alike or different and W and W' may be alike or different, and are as defined above.

Examples of compounds falling within this scope of the invention include:

4,7,9-Trihydroxy-6-(iminomethyl)-1-phenazinecarboxamide.

4,7,9-Trihydroxy-6-(iminomethyl)-8-methyl-1-phenazinecarboxamide.

4,7,9-Trihydroxy-N-methyl-6-[(methylimino)methyl]-1-phenazinecarboxamide.

4,7,9-Trihydroxy-N,8-dimethyl-6-[(methylimino)methyl]-1-phenazinecarboxamide.

N-(2-Aminoethyl)-6-[[(2-aminoethyl)imino]methyl]-4,7,9-trihydroxy-1-phenazinecarboxamide.

N-(2-Aminoethyl)-6-[[(2-aminoethyl)imino]methyl]-4,7,9-trihydroxy-8-methyl-1-phenazinecarboxamide.

N-[2-(Dimethylamino)ethyl]-6-[[[2-(dimethylamino)ethyl]imino]methyl-4,7,9-trihydroxy-1-phenazinecarboxamide.

N-[2-(Dimethylamino)ethyl]-6-[[[2-(dimethylamino)ethyl]imino]methyl]-4,7,9-trihydroxy-8-methyl-1-phenazinecarboxamide.

N-[2-(Dimethylamino)ethyl-6-[[[2-(diethylamino)ethyl]imino]methyl]-4,7,9-trihydroxy-1-phenazinecarboxamide.

N-[2-(Diethylamino)ethyl]-6-[[[2-(diethylamino)ethyl]imino]methyl-4,7,9-trihydroxy-8-methyl-1-phenazinecarboxamide.

N-[3-(Dimethylamino)propyl]-6-[[[3-(dimethylamino)propyl]imino]methyl]-4,7,9-trihydroxy-1-phenazinecarboxamide.

N-[3-(Dimethylamino)propyl]-6-[[[3-(dimethylamino)propyl]imino]methyl]-4,7,9-trihydroxy-8-methyl-phenazinecarboxamide.

N-[2-[Bis(hydroxyethyl)amino]ethyl]-6-[[[2-[bis(hydroxyethyl)amino]ethyl]imino]methyl]-4,7,9-trihydroxy-1-phenazinecarboxamide.

N-[2-[Bis(hydroxyethyl)amino]ethyl]-6-[[[2-[bis(hydroxyethyl)amino]ethyl]imino]methyl]-4,7,9-trihydroxy-8-methyl-1-phenazinecarboxamide.

4,7,9-Trihydroxy-N-[2-(1-pyrrolidinyl)ethyl]-6-[[[2-(1-pyrrolidinyl)ethyl]imino]methyl]-1-phenazinecarboxamide.

4,7,9-Trihydroxy-8-methyl-N-[2-(1-pyrrolidinyl)ethyl]-6-[[[2-(1-pyrrolidinyl)ethyl]imino]methyl]-1-phenazinecarboxamide.

N-[2-(Dimethylamino)ethyl]-6-[[[3-(dimethylamino)-2-hydroxypropyl]imino]methyl]-4,7,9-trihydroxy-1-phenazinecarboxamide.

N-[4-(Dimethylamino)cyclohexyl]-6-[[[4-(dimethylamino)cyclohexyl]imino]methyl]-4,7,9-trihydroxy-1-phenazinecarboxamide.

N-[4-(Dimethylamino)cyclohexyl-[[[4-(dimethylamino)cyclohexyl]imino]methyl]-4,7,9-trihydroxy-8-methyl-1-phenazine carboxamide.

N-[(1-Ethyl-2-pyrrolidinyl)methyl]-6-[[[(1-ethyl-2-pyrrolidinyl)methyl]imino]methyl]-4,7,9-trihydroxy-1-phenazinecarboxamide.

N-[(1-Ethyl-2-pyrrolidinyl)methyl]-6-[[[(1-ethyl-2-pyrrolidinyl)methyl]imino]methyl]-4,7,9-trihydroxy-8-methyl-1-phenazinecarboxamide.

4,7,9-Trihydroxy-N-[2-(1-methyl-2-pyrrolidinyl)ethyl]-6-[[[2-(1-methyl-2-pyrrolidinyl)ethyl]imino]methyl]-1-phenazinecarboxamide.

4,7,9-Trihydroxy-8-methyl-N-[2-(1-methyl-2-pyrrolidinyl)ethyl]-6-[[[2-(1-methyl-2-pyrrolidinyl)ethyl]imino]methyl]-1-phenazinecarboxamide.

4,7,9-Trihydroxy-N-(1-methyl-4-piperidinyl)-6-[[(1-methyl-4-piperidinyl)imino]methyl]-1-phenazinecarboxamide.

4,7,9-Trihydroxy-8-methyl-N-(1-methyl-4-piperidinyl)-6-[[(1-methyl-4-piperidinyl)imino]methyl]-1-phenazinecarboxamide.

N-[5-(Dimethylamino)pentyl]-6-[[[5-(dimethylamino)pentyl]imino]methyl]-4,7,9-trihydroxy-1-phenazinecarboxamide.

N-[5-(Dimethylamino)pentyl]-6-[[[5-(dimethylamino)pentyl]imino]methyl]-4,7,9-trihydroxy-8-methyl-1-phenazinecarboxamide.

4,7,9-Trihydroxy-N-[2-[(2-methylpropyl)amino]ethyl]-6-[[[2-[(2-methylpropyl)amino]ethyl]imino]methyl]-1-phenazinecarboxamide.

4,7,9-Trihydroxy-8-methyl-N-[2-[(2-methylpropyl)amino]ethyl]-6-[[[2-[(2-methylpropyl)amino]ethyl]imino]methyl]-1-phenazinecarboxamide.

N-[2-(Diethylamino)ethyl]-6-[[[2-(Diethylamino)ethyl]imino]methyl]-4,7,9-trihydroxy-1-phenazinecarboxamide.

N-[2-(Diethylamino)ethyl]-6-[[[2-(Diethylamino)ethyl]imino]methyl]-4,7,9-trihydroxy-8-methyl-1-phenazinecarboxamide.

4,7,9-Trihydroxy-N-[2-(methylamino)ethyl]-6-[[[2-(methylamino)ethyl]imino]methyl]-1-phenazinecarboxamide.

4,7,9-Trihydroxy-8-methyl-N-[2-(methylamino)ethyl]-6-[[[2-(methylamino)ethyl]imino]methyl]-1-phenazinecarboxamide.

4,7,9-Trihydroxy-N-[2-[(2-hydroxyethyl)amino]ethyl]-6-[[[2-[(2-hydroxyethyl)amino]ethyl]imino]methyl]-1-phenazinecarboxamide.

4,7,9-Trihydroxy-N-[2-[(2-hydroxyethyl)amino]ethyl]-6-[[[2-[(2-hydroxyethyl)amino]ethyl]imino]methyl]-8-methyl-1-phenazinecarboxamide.

N-[2-(ethylmethylamino)ethyl]-6-[[[2-(ethylmethylamino)ethyl]imino]methyl]-4,7,9-trihydroxy-1-phenazinecarboxamide.

N-[2-(ethylmethylamino)ethyl]-6-[[[2-(ethylmethylamino)ethyl]imino]methyl]-4,7,9-trihydroxy-8-methyl-1-phenazinecarboxamide.

N-[2-(Dimethylamino)ethyl]-6-[[[3-(dimethylamino)-2-hydroxypropyl]imino]methyl]-4,7,9-trihydroxy-8-methyl-1-phenazinecarboxamide.

In accordance with another subgeneric chemical compound aspect, compounds of the present invention include amides of Formula V where Y', $R_4'$, and $R_5'$ have the values given above.

Examples of compounds falling within this embodiment include:

6-Formyl-4,7,9-trihydroxy-1-phenazinecarboxamide.

6-Formyl-4,7,9-trihydroxy-8-methyl-1-phenazinecarboxamide.

6-Formyl-4,7,9-trihydroxy-N-methyl-1-phenazinecarboxamide.

6-Formyl-4,7,9-trihydroxy-N,8-dimethyl-1-phenazinecarboxamide.

N-(2-Aminoethyl)-6-formyl-4,7,9-trihydroxy-1-phenazinecarboxamide.

N-(2-Aminoethyl)-6-formyl-4,7,9-trihydroxy-8-methyl-1-phenazinecarboxamide.

N-[2-(Dimethylamino)ethyl]-6-formyl-4,7,9-trihydroxy-1-phenazinecarboxamide.

N-[2-(Dimethylamino)ethyl]-6-formyl-4,7,9-trihydroxy-8-methyl-1-phenazinecarboxamide.

N-[3-(Dimethylamino)propyl]-6-formyl-4,7,9-trihydroxy-1-phenazinecarboxamide.

N-[3-(Dimethylamino)propyl]-6-formyl-4,7,9-trihydroxy-8-methyl-1-phenazinecarboxamide.

N-[2-[Bis(hydroxyethyl)amino]ethyl]-6-formyl-4,7,9-trihydroxy-1-phenazinecarboxamide.

N-[2-[Bis(hydroxyethyl)amino]ethyl]-6-formyl-4,7,9-trihydroxy-8-methyl-1-phenazinecarboxamide.

6-Formyl-4,7,9-trihydroxy-N-[2-(1-pyrrolidinyl)ethyl]-1-phenazinecarboxamide.

6-Formyl-4,7,9-trihydroxy-8-methyl-N-[2-(1-pyrrolidinyl)ethyl]-1-phenazinecarboxamide.

N-[4-(Dimethylamino)cyclohexyl]-6-formyl-4,7,9-trihydroxy-1-phenazinecarboxamide.

N-[4-(Dimethylamino)cyclohexyl]-6-formyl-4,7,9-trihydroxy-8-methyl-1-phenazinecarboxamide.

6-Formyl-4,7,9-trihydroxy-N-[2-(1-methyl-2-pyrrolidinyl)ethyl]-1-phenazinecarboxamide.

6-Formyl-4,7,9-trihydroxy-8-methyl-N-[2-(1-methyl-2-pyrrolidinyl)ethyl]-1-phenazinecarboxamide.

6-Formyl-4,7,9-trihydroxy-N-(1-methyl-4-piperidinyl)-1-phenazinecarboxamide.

6-Formyl-4,7,9-trihydroxy-8-methyl-N-(1-methyl-4-piperidinyl)-1-phenazinecarboxamide.

N-[5-(Dimethylamino)pentyl]-6-formyl-4,7,9-trihydroxy-1-phenazinecarboxamide.

N-[5-(Dimethylamino)pentyl]-6-formyl-4,7,9-trihydroxy-8-methyl-1-phenazinecarboxamide.

6-Formyl-4,7,9-trihydroxy-N-[2-[(2-methylpropyl)amino]ethyl]-1-phenazinecarboxamide.

6-Formyl-4,7,9-trihydroxy-8-methyl-N-[2-[(2-methylpropyl)amino]ethyl]-1-phenazinecarboxamide.

N-[2-(Diethylamino)ethyl-6-formyl-4,7,9-trihydroxy-1-phenazinecarboxamide.

N-[2-(Diethylamino)ethyl-6-formyl-4,7,9-trihydroxy-8-methyl-1-phenazinecarboxamide.

6-Formyl-4,7,9-trihydroxy-N-[2-(methylamino)ethyl]-1-phenazinecarboxamide.

6-Formyl-4,7,9-trihydroxy-8-methyl-N-[2-(methylamino)ethyl]-1-phenazinecarboxamide.

6-Formyl-4,7,9-trihydroxy-N-[2-[(2-hydroxyethyl)amino]ethyl]-1-phenazinecarboxamide.

6-Formyl-4,7,9-trihydroxy-N-[2-[(2-hydroxyethyl)amino]ethyl]-8-methyl-1-phenazinecarboxamide.

N-[2-(Ethylmethylamino)ethyl]-6-formyl-4,7,9-trihydroxy-1-phenazinecarboxamide.

N-[2-(Ethylmethylamino)ethyl]-6-formyl-4,7,9-trihydroxy-8-methyl-1-phenazinecarboxamide.

Compounds in accordance with the present invention are prepared from the starting materials 6-formyl-4,7,9-trihydroxy-1-phenazinecarboxylic acid, methyl ester or from 6-formyl-4,7,9-trihydroxy-8-methyl-1-phenazinecarboxylic acid, methyl ester. The former compound, 6-formyl-4,7,9-trihydroxy-1-phenazinecarboxylic acid, methyl ester, is known variously in the chemical literature as lomofungin or lomondomycin and is produced in isolable quantities from fermentation broth mixtures containing the microorganism *Streptomyces lomondensis* NRRL 3252 as detailed in U.S. Pat. No. 3,359,165.

The latter compound, 6-formyl-4,7,9-trihydroxy-8-methyl-1-phenazinecarboxylic acid, methyl ester, is produced in isolable quantities from fermentation broth mixtures containing the microorganism *Streptomyces galanosa*, designated NRRL 15738 as described more fully below in Example 1.

Higher alkyl esters derived from the two starting methyl esters are obtained by conventional transesterification reactions using the methyl esters as starting materials and followed, if necessary, by conventional hydrolysis of any acetal or hemiacetal formed at the 6-formyl functionality during the transesterification reaction.

The free acid forms of both compounds can be obtained by conventional basic hydrolysis of the methyl ester starting materials or the higher alkyl esters resulting from the transesterification in, for example, aqueous sodium hydroxide, followed by acidification.

Imine amide derivatives of Formula IV above are obtained, when $R_1$ is methyl, by reaction of 6-formyl-4,7,9-trihydroxy-8-methyl-1-phenazinecarboxylic acid, methyl ester with the desired amine, at a temperature of between about 25° C. and 100° C., preferably between about 30° C. and 70° C. Under these conditions, the Schiff base imine forms first as a result of the reaction between the amine and the formyl group at position six of the phenazine ring system. The carbomethoxy functionality of the imine thus formed reacts further with the amine reagent to produce the imine amide. The product to be isolated is then purified by conventional chemical methods.

When $R_1$ is hydrogen, the preceding reaction sequence does not produce the imine amide in significant quantities, presumably because of keto-enol tautomerism involving the hydrogen atom at position eight of the phenazine ring system and one of the adjacent phenolic groups. To prepare the imine amides of Structure IV above where $R_1$ is hydrogen, 6-formyl-4,7,9-trihydroxy-1-phenazinecarboxylic acid, formed by hydrolysis of the methyl ester starting material, is reacted with a coupling reagent such as 1,1'-carbonyldiimidazole or 1,3-dicyclohexylcarbodiimide in an anhydrous polar organic solvent such as dimethylformamide followed by the addition of the desired amine. The reaction is carried out at temperatures between about $-10°$ C. and 25° C. Under these conditions, if an excess of amine is used both the 6-formyl functionality and the carboxylic acid functionality are derivatized by reaction with the amine to produce the imine amide.

The imine ester compounds of Formula IIIa or IIIb above, where $R_3$ is alkoxy, are prepared by reacting the appropriate 6-formyl-4,7,9-trihydroxy-1-phenazine carboxylic acid ester or 6-formyl-4,7,9-trihydroxy-8-methyl-1-phenazinecarboxylic acid ester with the desired amine under mild conditions. For example, the esters may be reacted with the appropriate amine in a polar organic solvent such as tetrahydrofuran or dimethylformamide at room temperature for a few minutes, followed by isolation and purification of the product by conventional means.

Imine acids are prepared by reacting the 6-formyl-4,7,9-trihydroxy-1-phenazinecarboxylic acid or 6-formyl-4,7,9-trihydroxy-8-methyl-1-phenazinecarboxylic acid with the desired amine under mild conditions, or alternatively, by basic hydrolysis of the ester functionality of the corresponding imine esters with, for example, dilute aqueous sodium hydroxide, followed by acidification.

The amides of Formula Va and Vb above are prepared by acidic hydrolysis of the imino functionality of the imine amides, prepared as described above with, for example, dilute aqueous hydrochloric acid followed by isolation and purification of the amide product by conventional means.

Compounds of the present invention, form salts with a number of pharmaceutically acceptable inorganic bases and organic amines. Suitable inorganic bases include ammonium hydroxide and the hydroxides, carbonates, or bicarbonates of sodium, potassium, calcium, magnesium, iron, and zinc. Particularly preferred inorganic salts of compounds of the present invention are the sodium and potassium salts. Suitable organic amines for preparing base addition salts of acidic compounds of the present invention form a class of amines well known to practitioners of the pharmaceutical formulation art.

The salts are prepared by contacting the compounds with an equivalent amount of the desired base in the conventional manner. The compounds may be regenerated from the salts, if desired, by treating the salt with a dilute aqueous solution of an acid such as hydrochloric.

Compounds of the present invention, when $R_2$ and/or $R_3$ contain a basic nitrogen atom, form salts with a number of pharmaceutically acceptable inorganic and organic acids which include hydrochloric, hydrobromic, hydriodic, sulfuric, nitric, phosphoric, acetic, benzoic, citric, maleic, malic, tartaric, succinic, gluconic, ascorbic, sulfamic, oxalic, pamoic, methanesulfonic, benzenesulfonic, and related acids and mixtures thereof.

The acid addition salts may be made by mixing the free base form of the compound with the desired acid in a suitable solvent such as water or aqueous alcohol. The resulting solution may be evaporated or lyophilized to recover the salt which may then be purified by conventional methods.

The free base form of the compound may be recovered from the acid addition salt, if desired, by treating the salt with an aqueous solution of a suitable base such as sodium hydroxide, sodium carbonate, and the like.

The salts differ from the free base form of the compounds of this invention in such physical properties as melting point and solubility in polar solvents, but are otherwise considered equivalent for the purposes of this invention.

The compounds of the present invention and their pharmaceutically acceptable salts can exist in unsolvated as well as solvated forms, including hydrated forms. In general, the solvated forms with pharmaceutically acceptable solvents such as water, ethanol, and the like are considered equivalent to the unsolvated forms for the purposes of this invention.

The compounds of the present invention and their pharmaceutically acceptable salts are useful as antimicrobial agents. The antimicrobial activity of the representative examples of compounds in accordance with the present invention against five species of gram-negative bacteria, seven species of gram-positive bacteria, four species of yeast, and two species of fungi were determined using the microtiter dilution technique. This method is described by T. B. Conrath, "Handbook of Microtiter Procedures," Dynatech Corp., Cambridge, Mass., USA (1972); and T. L. Gavan et al, "Microdilution Test Procedures," in *Manual of Clinical Microbiology*, E. H. Lennette, Ed., American Soc. for Microbiol., Washington, D.C., U.S.A. (1980).

Each agent is suspended in a nonaqueous solvent for several minutes to sterilize the compound or, if the compound is completely soluble in water, the aqueous solution is sterilized by passage through a 0.2–0.45 micrometer membrane filter.

Each well of a sterile 96-well microdilution tray is filled under aseptic conditions with 0.1 ml of Mueller-Hinton broth (for antibacterial tests), or yeast extract-peptone-dextrose or buffered supplemented yeast nitrogen base (for tests with yeasts or fungi).

A 0.5-ml sample of the test compound solution is added to each of the eight wells in the first row of the tray. A microdilutor apparatus is used to simultaneously mix the contents of these wells and to transfer aliquots to each succeeding row of cells to obtain a range of serially diluted solutions. The last row of wells is untreated and serves as a control.

Each well containing broth and test compound is inoculated with about ten microliters of inoculum of the test microorganism. One well in the last row of wells (which is free of test compound) is not inoculated and is used as a sterility control. The trays are sealed and incubated at 37° C. for 16–24 hours (for bacteria) or at 28° C. for 36–48 hours (yeasts or fungi). During incubation, the inoculated medium is shaken at 100–140 rpm to increase contact between the microorganism cells and test compounds.

After the incubation period, each plate is evaluated by determining the lowest concentration of test compound required to inhibit the growth of the microorganism and recorded as a minimal inhibitory concentration (MIC). MIC values of <0.005 mg/ml to 0.333 mg/ml indicate antimicrobial activity; values of 0.333–1.0 mg/ml are considered indicative of marginal activity; and MIC values of >1.0 mg/ml are considered indicative of lack of activity against a particular microorganism.

The results of these tests appear in Table 1.

TABLE 1

| | Antimicrobial Activity Minimal Inhibitory Concentration (mg/ml) For Compound of Example: | | | | | | | |
|---|---|---|---|---|---|---|---|---|
| Microorganisms | 3 | 5 | 7 | 8 | 11 | 14 | 16 | 18 |
| *Escherichia coli* (PD-04863) | >1.000 | 0.0123 | 0.111 | 1.000 | 0.111 | 0.111 | 0.037 | 0.037 |
| *Salmonella typhimurium* | 1.000 | 0.0123 | 0.333 | 0.111 | 0.111 | 0.111 | 0.037 | 0.111 |
| *Alcaligenes viscolactis* | 0.333 | 0.0041 | 0.0041 | 0.0041 | 0.0123 | 0.0123 | 0.0123 | 0.0123 |
| *Branhamella catarrhalis* | 0.111 | 0.0014 | 0.0123 | 0.0041 | 0.0123 | 0.0123 | 0.0123 | 0.0123 |
| *Pseudomonas aeruginosa* | >1.000 | 0.111 | <1.000 | >1.000 | 1.000 | 1.000 | 0.333 | >1.000 |
| *Micrococcus luteus* | 0.111 | 0.0041 | 0.037 | 1.000 | 0.111 | 0.111 | 0.0123 | 0.0123 |
| *Staphylococcus aureus* | >1.000 | 0.0123 | 0.333 | 1.000 | 0.037 | 0.037 | 0.037 | 0.037 |
| *Streptococcus pyogenes* | 0.111 | 0.0041 | 0.111 | 1.000 | 0.111 | 0.111 | 0.037 | 0.037 |
| *Streptococcus pneumoniae* | <0.00046 | <0.00046 | 0.037 | 1.000 | 0.111 | 0.111 | 0.037 | 0.037 |
| *Streptococcus faecalis* | 1.000 | 0.0123 | 1.000 | >1.000 | 0.111 | 0.111 | 0.111 | 0.037 |

TABLE 1-continued

| | Antimicrobial Activity Minimal Inhibitory Concentration (mg/ml) For Compound of Example: | | | | | | | |
|---|---|---|---|---|---|---|---|---|
| Microorganisms | 3 | 5 | 7 | 8 | 11 | 14 | 16 | 18 |
| Bacillus cereus | 0.333 | 0.0014 | 0.111 | 0.037 | 0.037 | 0.037 | 0.0123 | 0.0123 |
| Bacillus megaterium | 1.000 | 0.0041 | 0.333 | 1.000 | 0.111 | 0.111 | 0.037 | 0.037 |
| Saccharomyces cerevisiae | >1.000 | 0.111 | 1.000 | >1.000 | 0.111 | >1.000 | 0.111 | 0.111 |
| Schizosaccharomyces pombe | >1.000 | 0.037 | 0.111 | >1.000 | 0.037 | 0.111 | 0.037 | 0.037 |
| Rhodotorula aurantiaca | >1.000 | 0.111 | 0.111 | >1.000 | 0.0123 | 0.037 | 0.037 | 0.037 |
| Torulopsis albida | 1.000 | 0.333 | 1.000 | >1.000 | 0.111 | 0.333 | 0.037 | 0.037 |
| Mucor paraciticus | 1.000 | 0.037 | 0.333 | >1.000 | 0.037 | 0.333 | 0.111 | 0.037 |
| Rhizopus japonicus | >1.000 | 0.111 | 0.333 | >1.000 | 0.037 | 0.333 | 0.111 | 0.037 |

The compounds of the present invention are also useful for inhibiting the growth of neoplasma in mammals by virtue of their cytotoxic activity against such neoplastic growths.

The antineoplastic activities of representative compounds of the present invention against the L1210 murine leukemia cell line in vitro were determined using the methods detailed by R. I. Geran et al, "Protocols for Screening Chemical Agents and Natural Products Against Animal Tumors and Other Biological Systems," 3rd Edition, *Cancer Chemotherapy Reports*, Part 3, Vol. 3, pages 1-87 (1972) which is incorporated herein by reference.

From duplicate tests, the cytotoxic activities were shown to be those given in Table 2. The $IC_{50}$ values are the concentration of compound required to produce 50% inhibition of growth of the cell line.

TABLE 2

| Cytotoxic Activity Against L1210 Murine Leukemia In Vitro | |
|---|---|
| Compound of Example | $IC_{50}$ (micrograms/ml) |
| 3 | 0.17 |
| 5 | 0.17 |
| 7 | 0.63 |
| 8 | 0.24 |
| 11 | 3.47 |
| 16 | 0.33 |
| 18 | 0.24 |

The in vivo antineoplastic activity of representative compounds of the present invention against the transplanted P388 leukemia cell line in mice was determined in accordance with the protocol given in Geran et al, cited above.

The mice were infected intraperitoneally on Day 0 and then administered the indicated doses of the test compounds on Days 1-9. The data are presented in Table 3.

TABLE 3

| Cytotoxic Activity Against P388 Murine Leukemia In Vivo % T/C* (Dosage; mg/kg/injection) For Compound of Example Number | | | | | | | |
|---|---|---|---|---|---|---|---|
| 3 | 5 | 7 | 8 | 9 | 11 | 16 | 18 |
| Toxic (25) | 137 (150) | 166 (200) | 205 (25) | 219 (80) | 213 (150) | 132 (100) | |
| 149 (12.5) | 113 (75) | 152 (100) | 146 (12.5) | 170 (40) | 166 (75) | 123 (50) | |
| 130 (6.25) | 104 (37.5) | 140 (50) | 129 (6.25) | 144 (20) | 147 (37.5) | 106 (25) | |
| 119 (3.12) | | 126 (25) | 113 (3.12) | 143 (10) | 136 (19) | | |
| | | | | 139 (5) | | | |

*% T/C = $\frac{\text{(Median survival time of treated mice)}}{\text{(Median survival time of untreated mice)}} \times 100$ For use as antimicrobial or antineoplastic agents, the compounds of the present invention are formulated together with a compatible and pharmaceutically acceptable carrier in a form appropriate for the desired route of administration. Examples of such forms include solid forms for oral administration such as tablets, pills, powders, and granules, liquid forms for topical or oral administration such as solutions, emulsions, elixirs, and syrups, and forms suitable for parenteral administration such as sterile solutions, suspensions, or emulsions.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided solid of the active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 0.1 mg to 500 mg preferably to 5 to 100 mg according to the particular application and the potency of the active ingredient. The compositions can, if desired, also contain other compatible therapeutic agents.

In therapeutic use, the mammalian dosage range for a 70 kg subject is from 1 to 1500 mg/kg of body weight per day or preferably 2 to 750 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

For use as antimicrobial agents, the compositions are administered so that the concentration of the active component exceeds that required for the minimal inhibition of the particular microorganism sought to be controlled.

For use in inhibiting the growth of neoplasms in a mammal, the compositions are administered parenterally in a daily dose which exceeds the minimal concentration required for cytotoxicity of the particular neoplastic tissue sought to be controlled.

The following examples are provided to enable one skilled in the art to practice the present invention. These examples are not to be read as limiting the scope of the invention as it is defined by the appended claims, but merely as illustrative thereof.

EXAMPLE 1

Fermentative production of 6-formyl-4,7,9-trihydroxy-8-methyl-1-phenazinecarboxylic acid, methyl ester-50 liter scale The actinomycete organism of the present invention which produces 6-formyl-4,7,9-trihydroxy-8-methyl-1-phenazinecarboxylic acid, methyl ester was obtained from a soil sample collected in the Virgin Islands. The organism was isolated from the soil sample by standard plating techniques using a suitable agar medium containing inorganic salts such as sodium chloride, calcium carbonate, magnesium sulfate, and ferrous sulfate, carbon substrates such as glycerol, and nitrogen sources such as L-arginine. The organism was plated onto the agar medium and incubated at a favorable temperature, particularly 33° C., to allow for development of the organism The microorganism has been designated: *Streptomyces galanosa* (NRRL 15738) A comparison of the morphological characteristics and carbon utilization of the microorganism of this invention and those of *Streptomyces lomondensis* (NRRL 3252) disclosed in U.S. Pat. No. 3,359,165 appears in Tables 4 and 5, respectively.

TABLE 4

| Property | *Streptomyces galanosa* (NRRL 15738) | *Streptomyces lomondensis* (NRRL 3252) |
|---|---|---|
| Cell wall ornamentation | Rough to warty | Spiny |
| Whole Cell analysis | L,L-Diaminopimelic acid, no characteristic sugar | L,L-Diaminopimelic acid, no characteristic sugar |
| Spore chain morophology | Long, tight spirals, few open and straight spirals | Mostly straight and open spirals, few tight spirals |
| Gelatin liquefaction | Positive-brown | Positive-brown |
| Milk coagulation | Negative | Negative |
| Milk peptonization | Negative-brown pigment | Negative-light brown pigment |
| Reduction of nitrate | Positive | Negative |
| Melanine production or soluble pigments | ISP1-Positive ISP6-Positive ISP2-Light tan ISP3-Pearl pink | ISP1-Negative ISP6-Positive ISP2-Russet orange ISP3-Pearl pink |

TABLE 4-continued

| Property | Streptomyces galanosa (NRRL 15738) | Streptomyces lomondensis (NRRL 3252) |
|---|---|---|
| | ISP4-Colorless | ISP4-Pastel orange |
| | ISP5-Colorless | ISP5-Pastel orange |
| | CIM23-Light tan | CIM23-Light tan |
| Aerial mycelia | ISP2-Aqua grey | ISP2-Aqua grey |
| | ISP3-Slight white | ISP3-Slight aqua grey |
| | ISP4-Aqua grey | ISP4-Aqua grey |
| | ISP5-Aqua grey | ISP5-Aqua grey |
| | CIM23-Aqua grey | CIM23-Aqua grey |
| Substratal mycelia | ISP2-Clove brown | ISP2-Brown mahogany |
| | ISP3-Butterscotch | ISP3-Maple |
| | ISP4-Coffee | ISP4-Dark brown |
| | ISP5-Orange rust | ISP5-Wine |
| | CIM23-Clove brown | CIM23-Clove brown |

TABLE 5

| Substrate | Streptomyces galanosa (NRRL 15738) | Streptomyces lomondensis (NRRL 3252) |
|---|---|---|
| L-Arabinose | + | + |
| D-Fructose | + | + |
| D-Galactose | + | + |
| D-Glucose | + | + |
| i-Inositol | + | + |
| Inulin | + | + |
| Maltose | + | + |
| D-Mannitol | + | + |
| Melobiose | + | + |
| Raffinose | + | + |
| Rhamnose | + | + |
| Salicin | − | − |
| Sucrose | + | + |
| D-Xylose | + | + |

A culture of *Streptomyces galanosa* NRRL 15738, the microorganism of the present invention, has been deposited under the terms of the Budapest Treaty for the Deposit of Microorganisms with the Northern Regional Research Laboratory of the United States Department of Agriculture, Peoria, Ill. 61604, where it is being maintained in their permanent culture collection. The deposit has been designated NRRL 15738.

This microorganism is also maintained as a dormant culture in lyophile tubes, in cryogenic vials, and in soil sample tubes in the Warner-Lambert/Parke-Davis Culture Collection, 2800 Plymouth Rd., Ann Arbor, Mich. 48105, where it bears the deposit designation WP-4611.

The compound, 6-formyl-4,7,9-trihydroxy-8-methyl-1-phenazinecarboxylic acid, methyl ester, which exhibits both antimicrobial and antitumor activity is produced in isolable quantities by isolate NRRL 15738 during aerobic fermentation under controlled conditions. The fermentation medium consists of sources of carbon, nitrogen, minerals, and growth factors. Examples of suitable carbon sources are glycerol and various simple sugars such as glucose, mannose, fructose, xylose, ribose, or other carbohydrate-containing substances such as dextrin, starch, corn meal, and whey. The normal quantity of carbon source material in the culture medium generally varies between about 0.1 to 10 weight percent.

Suitable nitrogen sources for the culture medium include inorganic or mixed inorganic-organic nitrogenous compounds. Examples of such materials are cottonseed meal, soybean meal, corn germ flour, corn steep liquor, distiller solubles, peanut meal, peptonized milk, and various ammonium salts.

The addition of minerals and growth factors to the fermentation broth is also helpful in the fermentative production of 6-formyl-4,7,9-trihydroxy-8-methyl-1-phenazinecarboxylic acid, methyl ester by isolate NRRL 15738. Examples of suitable minerals for the culture medium are potassium dihydrogen phosphate, sodium chloride, ferrous sulfate, calcium carbonate, cobalt chloride, and zinc sulfate. Growth factors are provided by such sources as various yeast and milk by-products.

The preferred method of producing 6-formyl-4,7,9-trihydroxy-8-methyl-1-phenazinecarboxylic acid, methyl ester in accordance with the present invention is by submerged culture fermentation of a nutrient broth by isolate NRRL 15738. According to this embodiment of the invention, the fermentation medium ingredients are prepared in suspension and the resulting suspension is adjusted to a pH value preferably between about pH 4 and pH 8. The culture medium is then sterilized by autoclaving or steam heating, cooled to a suitable temperature between 16° and 45° C., and then inoculated with the microorganism.

Fermentation is then carried out with aeration and agitation until isolable quantities of 6-formyl-4,7,9-trihydroxy-8-methyl-1-phenazinecarboxylic acid, methyl ester are produced, usually within two to ten days under these conditions.

In the submerged culture method, fermentation is carried out in shake-flasks or in stationary tank fermentors. In shake-flasks, aeration is effected by agitation of the flasks, causing efficient mixing of the inoculated medium with air. In stationary tank fermentors, agitation is provided by impellers in the form of disk turbines, vaned discs, open turbines, or marine propellors. Aeration is provided by sparging air or oxygen into the fermentation mixture during agitation.

Isolate NRRL 15738 in its dormant state was transferred to an agar slant tube containing sterile CIM 23 culture medium and incubated for 7 to 14 days at 28° C.

TABLE 6

| Composition of CIM 23 Culture Medium | |
|---|---|
| Amidex Corn Starch | 20 g |
| N-Z Amine, Type A | 2 g |
| Beef Extract (Difco) | 1 g |
| Yeast Extract (Difco) | 1 g |
| Cobaltous chloride hexahydrate | 20 mg |
| Agar | 20 g |
| Distilled water | 1000 ml |

A portion of the resulting microbial growth was used to inoculate an 18×150 mm tube containing 5 ml of SD-05 culture medium. The seed tube culture was shaken at 33° C. on a rotary gyratory shaker at 170 rpm for three to four days.

TABLE 7

| Composition of SD-05 Culture Medium | |
|---|---|
| Yeast Extract (Amberex 1003) | 5 g |
| Glucose monohydrate (cerelose) | 1 g |
| Dextrin (Amidex B 411, Corn Products Co.) | 24 g |
| Casein Digest (N-Z Case, Sheffield) | 5 mg |
| Spray-dried Meat Solubles (Daylin Labs) | 3 g |
| Calcium carbonate | 2 g |

TABLE 7-continued

| Composition of SD-05 Culture Medium | |
| --- | --- |
| Distilled Water | 1000 ml |

A 1-ml portion of the microbial growth from the seed tube was transferred to a 38×200 mm shake-tube containing 25 ml of PM-12 screening medium. The PM-12 screening medium consisted of a water suspension of 1% dextrin and 1% by weight of a feed grade mixture composed of soybean meal, ground yellow corn, ground wheat, corn gluten meal, wheat middlings, dried milk products, animal fat preserved with BHA, ground beet pulp, calcium carbonate, sucrose, dehydrated alfalfa meal, dicalcium phosphate, brewer's dried yeast, salt, vitamin $B_{12}$ supplement, riboflavin supplement, calcium pantothenate, niacin, choline chloride, menadione sodium bisulfite (source of vitamin K activity), folic acid, pyridoxine hydorchloride, thiamin, ascorbic acid, vitamin A supplement, vitamin D activated animal sterol (source of vitamin $D_3$), vitamin E supplement, iron carbonate, iron sulfate, calcium iodate, manganous oxide, copper oxide, cobalt carbonate, and zinc oxide.

The inoculated shake-tube was incubated for three days at 33° C. on a gyratory shaker at 170 rpm (5 cm throw). The production of 6-formyl-4,7,9-trihydroxy-8-methyl-1-phenazinecarboxylic acid, methyl ester was monitored by screening the fermentation broth against *Escherichia coli* (PD-08000).

*E. coli* (PD-08000) was seeded onto agar plates and 6.35 mm diameter paper discs impregnated with the fermentation beer were laid on the inoculated medium and incubated at 37° C. overnight. The diameters of the zones of inhibition around the paper discs indicated the relative concentration of 6-formyl-4,7,9-trihydroxy-8-methyl-1-phenazinecarboxylic acid, methyl ester in the fermentation broth.

Isolate NRRL 15738 was used to inoculate a 2-liter baffled Erlenmeyer flask containing 600 ml of SD-05 culture medium. The flask contents were incubated at 33° C. for 65–75 hours. The resulting microbial growth was used to inoculate 16 liters of SD-05 culture medium contained in a 30-liter stirred-jar fermentor. The contents of the stirred jar were incubated at 33° C. for 24 hours with stirring and air sparging at a rate of one volume/volume/minute. The resulting microbial growth was used to inoculate four production scale stirred jar fermentors.

Four 30-liter stirred-jar fermentors, each containing about 16 liters of PM-12 culture medium were sterilized by autoclaving for 90 minutes at 121° C. The jar contents were then cooled to 33° C. and then inoculated with 800 ml of inoculum from the previously described batch. The four jars were subsequently incubated at 33° C. for three days while being stirred and sparged with air at a rate of one volume/volume/minute. The production of 6-formyl-4,7,9-trihydroxy-8-methyl-1-phenazinecarboxylic acid, methyl ester was monitored throughout this fermentation by assay against *E. coli* (PD-08000) as described above. The data for these assays appear in Table 8.

TABLE 8

Microbial Assay of Fermentative Production of 6-Formyl-4,7,9-trihydroxy-8-methyl-1-phenazinecarboxylic acid, Methyl Ester

| Time (hours) | pH | Sedimentation Value (Percent Growth) | Inhibition Zone Diameter (mm) for 12.7 mm Disk vs. *Escherichia coli* (PD-08000) |
| --- | --- | --- | --- |
| Jar 1 | | | |
| 0 | 6.6 | — | 0 |
| 27 | 6.3 | 6.0 | 24 |
| 50 | 6.4 | 4.7 | 23 |
| 71 | 7.2 | 4.7 | 23 |
| Jar 2 | | | |
| 0 | 6.6 | — | 0 |
| 27 | 6.35 | 6.7 | 23 |
| 50 | 6.6 | 4.7 | 22 |
| 71 | 7.2 | 5.3 | 25 |
| Jar 3 | | | |
| 0 | 6.6 | — | 0 |
| 27 | 6.2 | 5.3 | 23 |
| 50 | 6.4 | 4.7 | 22 |
| 71 | 7.0 | 4.0 | 23 |
| Jar 4 | | | |
| 0 | 6.6 | — | 0 |
| 27 | 6.2 | 6.0 | 24 |
| 50 | 6.45 | 4.7 | 24 |
| 71 | 7.0 | 4.7 | 24 |

EXAMPLE 2

Fermentative production of 6-formyl-4,7,9-trihydroxy-8-methyl-1-phenazinecarboxylic acid, methyl ester—5000 liter scale A cryogenically preserved sample containing approximately 1 ml of *Streptomyces galanosa* NRRL 15738 culture was used to inoculate 600 ml of SD-05 seed medium contained in a two-liter baffled shake flask. The inoculated flask contents were incubated for 72 hours at 33° C. while being shaken on a gyrating shaker at 130 rpm.

After 72 hours, the contents of the seed flask were transferred aseptically to a 30-liter seed medium. The inoculated fermentor contents were incubated at 33° C. for 28 hours while being stirred at 300 rpm and sparged with air at a rate of 1 vol/vol/min.

The microbial growth from the above stainless steel fermentor was used to inoculate 75 gallons (284 liters) of SD-05 seed medium contained in a 200-gallon (757-liter) stainless steel fermentor. The medium was sterilized by steam heating at 121° C. for 40 minutes after which the fermentor and contents were cooled to 33° C. and inoculated with about 15 liters of the microoganism-containing broth. The resulting mixture was incubated at 33° C. for 23 hours while being stirred at 155 rpm and sparged with air at a rate of about 0.75 vol/vol/min.

After 23 hours the microbial growth from the above 200-gallon fermentor was used to inoculate 1300 gallons (4921 liters) of PM-13 nutrient medium contained in a 2000-gallon (7571-liter) stainless steel fermentor.

TABLE 9

| Composition of PM-13 Nutrient Medium | |
| --- | --- |
| Ammonium Sulfate (Allied Chemical) | 0.1% |
| Calcium Carbonate (Pfizer) | 0.4% |
| Pharmamedia (Traders Protein) | 2.0% |
| Cerelose (Atlas Sugar) | 2.0% |
| Maltrin (Grain Processing) | 2.0% |

TABLE 9-continued

Composition of PM-13 Nutrient Medium

No pH adjustment

The medium was sterilized prior to inoculation by heating with steam for 40 minutes at 121° C. After sterilization, the fermentor and contents were cooled to 33° C., inoculated, and incubated for 27 hours at 33° C. with stirring at 125 rpm and air sparging at a rate of 0.75 vol/vol/min.

As in Example 1, the progress of the fermentation was followed by periodically measuring pH, sedimentation vlues, and inhibition of the growth of E. coli (PD-08000). Additionally, the ability of the fermentation broth, at dilutions of 1:50 and 1:250, to inhibit the in vitro growth of the L1210 murine leukemia cells was measured at several points during the course of the fermentation. These data appear in Table 10.

TABLE 10

| Time (hrs) | pH | Sedimentation Value (Percent Growth) | Inhibition Zone Diameter (in mm, 12.7 mm disks) vs. E. Coli (PD 08000) | % Growth Inhibition of L1210 cells at 1:50 | 1:250 |
|---|---|---|---|---|---|
| 0 | 7.1 | 7.4 | — | — | — |
| 23 | 5.7 | 20.0 | 25 | 100% | 71% |
| 24 | 5.6 | 18.7 | 26 | 100% | 76% |
| 26 | 5.5 | 19.3 | 23 | 100% | 64% |
| 27 | 5.4 | 16.7 | 24 | 100% | 65% |

EXAMPLE 3

Isolation of 6-formyl-4,7,9-trihydroxy-8-methyl-1-phenazinecarboxylic acid, methyl ester The unfiltered beer (4763 liters) from Example 2 above was adjusted to pH 3.0 with 50% sulfuric acid. Celite 545 (660 kg) was added and the mixture was stirred for one hour with 3030 liters of ethyl acetate. Additional sulfuric acid was added to maintain the pH at 3.0. The mixture was then filtered and the filter cake was washed twice with 380-liter portions of ethyl acetate. The filtrate and washes were combined and the upper ethyl acetate layer was concentrated in vacuo to 337 liters. This concentrate was stored for 65 hours at −20° C. The precipitate that formed was filtered off, washed with three liters of ethyl acetate, four liters of methanol, and finally with 23.5 liters of chloroform to leave a solid that was dried in vacuo. This partially crystalline product (155 g) was recrystallized from 18 liters of chloroform:methanol (9:1) to afford 63 g of crystalline 6-formyl-4,7,9-trihydroxy-8-methyl-1-phenazinecarboxylic acid, methyl ester. Concentration and cooling of the mother liquor afforded an additional 23 g of crystalline product.

The product was analyzed by a high pressure liquid chromatographic (HPLC) method utilizing a 4.1 (ID)×250 mm PRP-1 column (Hamilton Co., Reno, Nev. 89510) and a mobile phase consisting of a linear gradient from 0.025 M pH 9.5 borate buffer: acetonitrile:methanol (90:5:5) at time zero to 0.025 M pH 9.5 borate buffer:acetonitrile:methanol (70:25:5) over a course of seven minutes at a flow rate of 2.0 ml/min. The retention time of the product in this system is 3.5 minutes.

EXAMPLE 4

Preparation of 6-formyl-4,7,9-trihydroxy-8-methyl-1-phenazinecarboxylic acid, methyl ester, potassium salt (phenolate salt)

6-Formyl-4,7,9-trihydroxy-8-methyl-1-phenazinecarboxylic acid, methyl ester (68.2 mg, 0.208 mmol) was suspended in 5 ml of water and a solution of 0.416 mmol of potassium hydroxide in 0.5 ml of water was added. The resulting red solution was lyophilized to produce 74.4 mg of 6-formyl-4,7,9-trihydroxy-8-methyl-1-phenazinecarboxylic acid, methyl ester potassium salt as a rust-colored solid.

EXAMPLE 5

Preparation of 6-[[[2-(dimethylamino)ethyl]imino]methyl]-4,7,9-trihydroxy-8-methyl-1-phenazinecarboxylic acid, methyl ester 6-Formyl-4,7,9-trihydroxy-8-methyl-1-phenazinecarboxylic acid, methyl ester (500 mg, 1.52 mmol) was suspended in 50 ml of tetrahydrofuran and 2-(dimethylamino)ethylamine (160 mg, 1.83 mmol) was added dropwise with stirring to produce a deep purple solution. After about 20 minutes at room temperature, an orange precipitate formed and the reaction mixture gradually developed an orange color.

The crude orange product was separated by filtration, washed with tetrahydrofuran, and dried under vacuum to yield 480 mg (80.3%) of 6-[[[2-(dimethylamino)ethyl]imino]methyl-4,7,9-trihydroxy-8-methyl-1-phenazinecarboxylic acid, methyl ester. The retention time for the product, employing the HPLC system and method described in Example 3 above was 5.2 minutes.

EXAMPLE 6

Preparation of 6-[[[2-(dimethylamino)ethyl]imino]methyl]-4,7,9-trihydroxy-8-methyl-1-phenazinecarboxylic acid, methyl ester, methanesulfonate salt 6-[[[2-(Dimethylamino)ethyl]imino]methyl]-4,7,9-trihydroxy-8-methyl-1-phenazinecarboxylic acid, methyl ester (468 mg, 1.177 mmol) was stirred at room temperature with methanesulfonic acid (125 mg, 1.3 mmol) in 20 ml of water until dissolution was complete.

The solution was diluted with water and lyophilized to yield the crude methanesulfonate salt which was washed with isopropyl alcohol, and filtered. The solid residue was dissolved in water and lyophilized to yield 423 mg of the purified salt.

EXAMPLE 7

Preparation of N-[2-(dimethylamino)ethyl]-6-[[[2-(dimethylamino)ethyl]imino]methyl]-4,7,9-trihydroxy-8-methyl-1-phenazinecarboxamide 6-Formyl-4,7,9-trihydroxy-8-methyl-1-phenazinecarboxylic acid, methyl ester (1.0 g, 3.05 mmol) was dissolved in 50 ml of anhydrous N,N-dimethylethylenediamine (Aldrich Chemical Co., Milwaukee, Wis., USA) and stirred at 55° C. for 145 minutes under a nitrogen atmosphere. The course of the reaction was followed by high pressure liquid chromatographic (HPLC) methods as described in Example 3.

After the reaction was complete, the excess N,N-dimethylethylenediamine was evaporated under vacuum and the residue was dissolved in 150 ml of water. The pH of this solution was adjusted to 4.5 with acetic acid and the resulting solution chromatographed over 300 ml of Diaion HP-20 resin (Mitsubishi Chem. Ind. Ltd., 5-2, Marunochi 2 Chiyodaku, Tokyo, Japan) which had been previously equilibrated with 0.075 M ammonium acetate buffer (pH 4.5).

The column was washed with two 600-ml portions of ammonium acetate buffer and then eluted with 200 ml portions of 5%, 10%, and 15% acetonitrile in buffer. The eluates were assayed by HPLC, and those containing the product were combined and the acetonitrile removed by evaporation under vacuum. The remaining solution was lyophilized. The lyophilate was triturated twice with 100-ml portions of chloroform. The chloroform solution was filtered and extracted twice with 100-ml portions of water. The aqueous extracts were combined, the excess chloroform removed by evaporation, and the aqueous solution lyophilized to yield 986 mg (2.31 mmol, 75.7%) of N-[2-(dimethylamino)ethyl]-6-[[[2(dimethylamino)ethyl]imino]methyl]-4, 7,9-trihydroxy-8-methyl-1-phenazinecarboxamide as a dark red, hygroscopic powder. The retention time of this product employing the HPLC system and method described in Example 3 above, was 5.6 minutes.

EXAMPLE 8

Preparation of N-[2-(dimethylamino)ethyl]-6-formyl-4, 7,9-trihydroxy-8-methyl-1-phenazinecarboxamide N-[2-(dimethylamino)ethyl]-6-[[[2-(dimethylamino)ethyl]imino]methyl]-4, 7,9-trihydroxy-8-methyl-1-phenazinecarboxamide (252 mg, 0.59 mmol) was dissolved in 50 ml of 0.3 M aqueous hydrochloric acid. The mixture was stirred for three hours at 55° C. and the course of the reaction was followed by the previously described HPLC methods.

When the reaction was complete, the mixture was diluted with 50 ml of 10% sodium chloride solution and 50 ml of 1.0 M sodium phosphate buffer (pH 7.0) and extracted twice with 50-ml portions of 1-butanol.

The butanol extracts were combined and washed with 20 ml of water. The extract was then concentrated under vacuum to remove excess water, and cooled to −20° C. for eighteen hours. Deep red crystals of the product formed, which were separated by filtration to yield 160 mg (0.42 mmol, 71%) of N-[2-(dimethylamino)ethyl]-6-formyl-4, 7,9-trihydroxy-8-methyl-1-phenazinecarboxamide, mp>250° C. The retention time, using the HPLC system and method described in Example 3, above, was 4.6 minutes.

EXAMPLE 9

Preparation of N-[2-(dimethylamino)ethyl]-6-formyl-4, 7,9-trihydroxy-8-methyl-1-phenazinecarboxamide, methanesulfonate salt N-[2-(Dimethylamino)ethyl]-6-formyl-4,7,9-trihydroxy-8-methyl-1-phenazinecarboxamide (5.75 g, 0.015 mole) was dissolved in 103 ml of 0.15 M methanesulfonic acid (Thiokol/Ventron) to give a clear red solution which was freeze-dried. The resulting orange-red solid was transferred to a sintered glass funnel and washed with three volumes of isopropyl alcohol (100, 75, and 100 ml). The solid residue was then redissolved in 150 ml of water, filtered, and freeze-dried to give 6.73 g (94%) of methanesulfonate salt as an orange solid.

EXAMPLE 10

Conversion of N-[2-(dimethylamino)ethyl]-6-formyl-4, 7,9-trihydroxy-8-methyl-1-phenazinecarboxamide methanesulfonate salt to alternative salt forms The methane sulfonate salt prepared above in Example 9 is dissolved in water and the pH adjusted to 5.5 with aqueous NaOH. After cooling at 5° C. overnight the free base form crystallizes from the solution and is collected by filtration, washed with acetonitrile, and dried in vacuo. The product thus formed is then treated with an aqueous solution containing one equivalent of the desired acid such as hydrochloric, gluconic, etc., and lyophilized to produce the new salt form.

EXAMPLE 11

Preparation of 6-formyl-4,7,9-trihydroxy-8-methyl-1-phenazinecarboxylic acid

6-Formyl-4,7,9-trihydroxy-8-methyl-1-phenazinecarboxylic acid, methyl ester (500 mg, 1.52 mmol) was suspended in 20 ml of 1 M aqueous sodium hydroxide solution and stirred at 60° C. for 1.2 hours.

The reaction mixture was acidified by dropwise addition of concentrated hydrochloric acid and the precipitate which formed was collected by filtration. The residue was partially dissolved in ethyl acetate:methanol and the mixture filtered. Upon standing at room temperature, crystals of 6-formyl-4, 7,9-trihydroxy-8-methyl-1-phenazinecarboxylic acid formed which were collected by filtration.

The residue which had not dissolved in ethyl acetate:methanol was dissolved in boiling chloroform: methanol and the solution filtered. Upon refrigeration, additional crystals of 6-formyl-4,7,9-trihydroxy-8-methyl-1-phenazinecarboxylic acid formed from the chloroform:methanol solution and were collected by filtration.

The two crops of crystals were combined to yield 150 mg of the acid. The retention time, employing the HPLC system and method of Example 3 above, was 1.0 minute.

EXAMPLE 12

Preparation of 6-formyl-4,7,9-trihydroxy-1-phenazinecarboxylic acid

6-Formyl-4,7,9-trihydroxy-1-phenazinecarboxylic acid, methyl ester (400 mg, 1.27 mmol), prepared as described in U.S. Pat. No. 3,359,165 was dissolved in 40 ml of 1 M aqueous sodium hydroxide solution and stirred for 145 minutes at 25° C., with the reaction being monitored by high pressure liquid chromatographic techniques as described above in Example 3. When the hydrolysis was complete, the solution was adjusted to pH 2.5 by the addition of 1 M HCl whereupon a red precipitate of crude 6-formyl-4,7,9trihydroxy-1-phenazinecarboxylic acid formed. After 15 minutes, the precipitate was collected by filtration, washed with water, and dried. The crude acid was recrystallized from 200 ml of 1:1 chloroform: methanol to yield 282 mg (0.94 mmol, 74%) of 6-formyl-4,7,9-trihydroxy-1-phenazinecarboxylic acid. The retention time, employing the HPLC system and method described above in Example 3, was 1.3 minutes.

EXAMPLE 13

Preparation of
N-[2-(dimethylamino)ethyl]-6-[[[2-(dimethylamino)ethyl]imino]methyl]-4,
7,9-trihydroxy-1-phenazinecarboxamide 6-Formyl-4,7,9-trihydroxy-1-phenazinecarboxylic acid (520 mg, 1.73 mmoles) was suspended in 15 ml of dry dimethylformamide (DMF) and 1,1'-carbonyldiimidazole (700 mg, 4.32 mmoles) dissolved in 4 ml of DMF was added. The reaction mixture was stirred for 20 minutes at 25° C. until a clear solution had formed. The solution was then cooled in an ice bath and N,N-dimethylethylenediamine (0.6 ml) added. After stirring for 15 minutes at 25° C. the excess reagents were removed under vacuum to yield N-[2-(dimethylamino)ethyl]-6-[[[2-(dimethylamino)ethyl]imino]methyl]-4, 7,9-trihydroxy-1-phenazinecarboxamide. The retention time for this product in the HPLC system described above in Example 3 is 5.0 minutes.

EXAMPLE 14

Preparation of
N-[2-(dimethylamino)ethyl]-6-formyl-4,7,9-trihydroxy-1-phenazinecarboxamide The imine amide prepared above in Example 13 was dissolved in 425 ml of water and the pH adjusted to 6.5 with hydrochloric acid. After heating to 45° C., 45 ml of concentrated hydrochloric acid was added slowly and the solution was stirred at 45° C. for 80 minutes, cooled, and extracted three times with ethyl acetate. The lower aqueous layer was concentrated in vacuo to remove residual organic solvent and then chromatographed over 100 ml of Diaion HP-20 resin. The column was washed with 500 ml of 0.01 M HCl then eluted with acetonitrile:0.01 M HCl (1:1). The eluate (50 ml) was diluted with 50 ml of acetonitrile:water (1:1) and the pH adjusted to 5.5 with 1 M aqueous NaOH and cooled to 5° C. After 18 hours the red precipitate which had formed was separated by filtration, washed with water and acetonitrile, and dried in vacuo to yield 530 mg of N-[2-(dimethylamino)ethyl]-6-formyl-4,7,9-trihydroxy-1-phenazinecarboxamide, which could be further purified by recrystallization from hot chloroform-methanol (1:1). This product has a retention time in the HPLC system described above in Example 3, of 2.9 minutes.

EXAMPLE 15

Preparation of
N-[2-(diethylamino)ethyl]-6-[[[2-(diethylamino)ethyl]imino]methyl]-4,7,9-trihydroxy-8-methyl-1-phenazinecarboxamide 6-Formyl-4,7,9-trihydroxy-8-methyl-1-phenazinecarboxylic acid, methyl ester (1.02 g, 3.02 mmol) was stirred at 65° C. for two hours with 50 ml of 2-(diethylamino)ethyl amine. When the reaction was complete, as determined by HPLC analysis in the previously described system, the excess amine was removed under vacuum to yield N-[2-(diethylamino)ethyl]-6-[[[2-(diethylamino)ethyl]imino]methyl]-4, 7,9-trihydroxy-1-phenazinecarboxamide. The retention time for this product using the system described above in Example 3 is 6.0 minutes.

EXAMPLE 16

Preparation of N-[2-(diethylamino)ethyl]-6-formyl-4,
7,9-trihydroxy-8-methyl-1-phenazinecarboxamide The imine amide product from Example 15 was dissolved in 50 ml of water and heated to 55° C. with stirring. Concentrated hydrochloric acid (6 ml) was added dropwise and the temperature of the mixture was slowly increased to 72° C. Hydrolysis of the imine functionality was essentially complete after two hours as indicated by HPLC analysis. The reaction mixture was heated for an additional hour, and then cooled in ice to produce the product as a yellow precipitate which was collected by filtration.

The solid residue was dissolved in 0.01 N HCl (5 ml) and chromatographed over HP-20 (100 ml, previously equilibrated with 0.01 N HCl). The column was washed with 0.01 N HCl (200 ml) and eluted with water-:acetonitrile (9:1, 100 ml) and water: acetonitrile (1:1, 100 ml). The eluates containing product were combined, concentrated in vacuo, then lyophilized to yield 925 mg of N-[2-(diethylamino)ethyl]-6-formyl-4,7,9-trihydroxy-1-phenazinecarboxamide. The retention time for this product in the HPLC system described above in Example 3 is 4.5 minutes.

EXAMPLE 17

Preparation of
N-[3-(dimethylamino)propyl]-6-[[[3-(dimethylamino)propyl]imino]methyl]-4,7,9-trihydroxy-8-methyl-1-phenazinecarboxamide 6-Formyl-4,7,9-trihydroxy-8-methyl-1-phenazinecarboxylic acid, methyl ester (1.107 g, 3.27 mmol), was stirred with 50 g of 3-(dimethylamino)propyl amine (Aldrich Chemical Company, Milwaukee, Wis., USA) at 60° C. for 1.5 hours. The reaction mixture was then cooled in an ice bath for 20 minutes and the crude imine amide product precipitated from solution. The precipitated solid was collected by filtration and washed with 50 ml of acetonitrile. The retention time for this product, employing the HPLC system and method described in Example 3 above, was 4.6 minutes.

EXAMPLE 18

Preparation of
N-[3-(dimethylamino)propyl]-6-formyl-4,
7,9-trihydroxy-8-methyl-1-phenazinecarboxamide An aqueous solution (50 ml) of the imine amide from Example 17 was stirred under a nitrogen atmosphere while 2 ml of concentrated hydrochloric acid was added in a dropwise manner. During the course of eight hours an additional 8 ml of concentrated hydrochloric acid (10 ml total) was added. The reaction mixture was then cooled in an ice bath and the solution saturated with sodium chloride to induce precipitation. The precipitated amide was collected by filtration and washed consecutively with acetonitrile and water. The residual orange solid was dissolved in water and chromatographed over HP-20 resin (50 ml, previously equilibrated with 0.01 N HCl). The column was washed with 0.01 N HCl, then eluted with 0.01 N HCl:acetonitrile (1:1). The eluate was adjusted to pH 5.5 with aqueous NaOH, concentrated in vacuo to remove the acetonitrile, and then lyophilized to give 530 mg of N-[3-(dimethylamino)propyl]-6-formyl-4,7,9-trihydroxy-8-methyl-1-phenazinecarboxamide. The retention time of this product, using the HPLC system described above in Example 3, is 3.6 minutes.

We claim:

1. A purified culture of *Streptomyces galanosa* NRRL 15738 which is capable of producing 6-formyl-4,7,9-trihydroxy-8-methyl-1-phenazinecarboxylic acid, methyl ester in isolable quantities under conditions of aerobic fermentation of a broth containing assimilable sources of carbon and nitrogen.

* * * * *